(12) United States Patent
Vasanthan et al.

(10) Patent No.: US 7,662,418 B2
(45) Date of Patent: *Feb. 16, 2010

(54) PREPARATION OF HIGH VISCOSITY BETA-GLUCAN CONCENTRATES

(75) Inventors: Thavaratnam Vasanthan, Edmonton (CA); Feral Temelli, Edmonton (CA); Zvonko Burkus, Edmonton (CA)

(73) Assignee: The Governors of the University of Alberta, Edmonton, AB ( * ) Notice: Subject to any disclaimer, the term of this patent is extended or adjusted under 35 U.S.C. 154(b) by 235 days.

This patent is subject to a terminal disclaimer.

(21) Appl. No.: 10/397,215

(22) Filed: Mar. 27, 2003

(65) Prior Publication Data

US 2004/0001907 A1 Jan. 1, 2004

Related U.S. Application Data

(63) Continuation-in-part of application No. 10/380,739, filed on Jul. 21, 2003, now Pat. No. 7,566,470.

(51) Int. Cl.
*A23L 1/10* (2006.01)
(52) U.S. Cl. .................. 426/436; 435/101; 426/615; 426/238; 426/429; 426/443; 426/52
(58) Field of Classification Search .......... 435/101; 426/615, 238, 429, 436, 443, 52
See application file for complete search history.

(56) References Cited

U.S. PATENT DOCUMENTS

| 5,183,677 | A | * | 2/1993 | Lehtomaki et al. | 426/436 |
| 5,518,710 | A | * | 5/1996 | Bhatty | 424/750 |
| 5,580,762 | A | * | 12/1996 | Karube et al. | 435/99 |
| 5,614,242 | A | * | 3/1997 | Fox | 426/549 |
| 5,725,901 | A | | 3/1998 | Fox | |
| 5,846,590 | A | * | 12/1998 | Malkki et al. | 426/443 |
| 6,083,547 | A | * | 7/2000 | Katta et al. | 426/443 |

FOREIGN PATENT DOCUMENTS

| EP | 747396 A1 * | 12/1996 |
| JP | 55118388 A * | 9/1980 |
| WO | WO 9702356 A1 * | 1/1997 |
| WO | WO 02/27011 | 4/2002 |
| WO | WO 02/28201 | 4/2002 |

OTHER PUBLICATIONS

Burkus, Z et al. Effect of extraction conditions on yield, composition, and viscosity stability of barley beta-glucan gum. Cereal Chem. 1998. 75(6): 805-809.*
Izydorczyk, MS et al. Variation in total and soluble beta-glucan content in hulless barley: Effects of thermal, physical, and enzymatic treatments. J. Agric. Food Chem. 2000. 48: 982-989.*
Temelli, F. Extraction and functional properties of barley beta-glucan as affected by temperature and pH. Journal of Food Science. 1997. 62(6): 1194-1197.*
Tunga, R et al. Some studies on optimization of extraction process for protease production in SSF. Bioprocess Engineering. 1999. 20: 485-489.*
Simon, LM et al. Stability of hydrolytic enzymes in water-organic solvent systems. Journal of Molecular Catalysis B: Enzymatic. 1998. 4: 41-45.*
Chitradon, L et al. Oligosaccharide synthesis by reversed catalysis using alpha-amylase from *Bacillus licheniformis*. Journal of Molecular Catalysis B: Enzymatic. 2000. 10: 273-280.*
Simon, LM et al. The effects of organic solvent/water mixtures on the structure and catalytic activity of porcine pepsin. Process Biochemistry. 2007. 42: 909-912.*
"Cardiovascular Disease Statistics" American Heart Association, 2000 (Online cited Nov. 23, 2000).
"The Changing Face of Heart Disease and Stroke in Canada 2000" Heart and Stroke Foundation of Canada, 2000. (Online, cited Nov. 29, 2000).
Kimura, T. Sugahara, T and Goto, M. 2000. Improvements of a method for production of konnyaku powder using ultrasonic treament. Journal of the Japanese Society for Food and Science and Technology (Nippon Shokuhin Kagaku Kogaku Kaishi). 47(8): 604-612.

* cited by examiner

*Primary Examiner*—Leon B. Lankford
*Assistant Examiner*—Susan E. Fernandez
(74) *Attorney, Agent, or Firm*—Squire, Sanders & Dempsey, L.L.P.

(57) ABSTRACT

This invention relates to methods for secondary processing of plant material and in particular for the recovery of valuable products such as fiber including beta-glucan, starch, and ethanol solubles from plant material containing starch and fiber. In particular, the invention relates to the preparation of high viscosity beta-glucan products through methods involving sonication/sonification and enzymes.

26 Claims, 2 Drawing Sheets

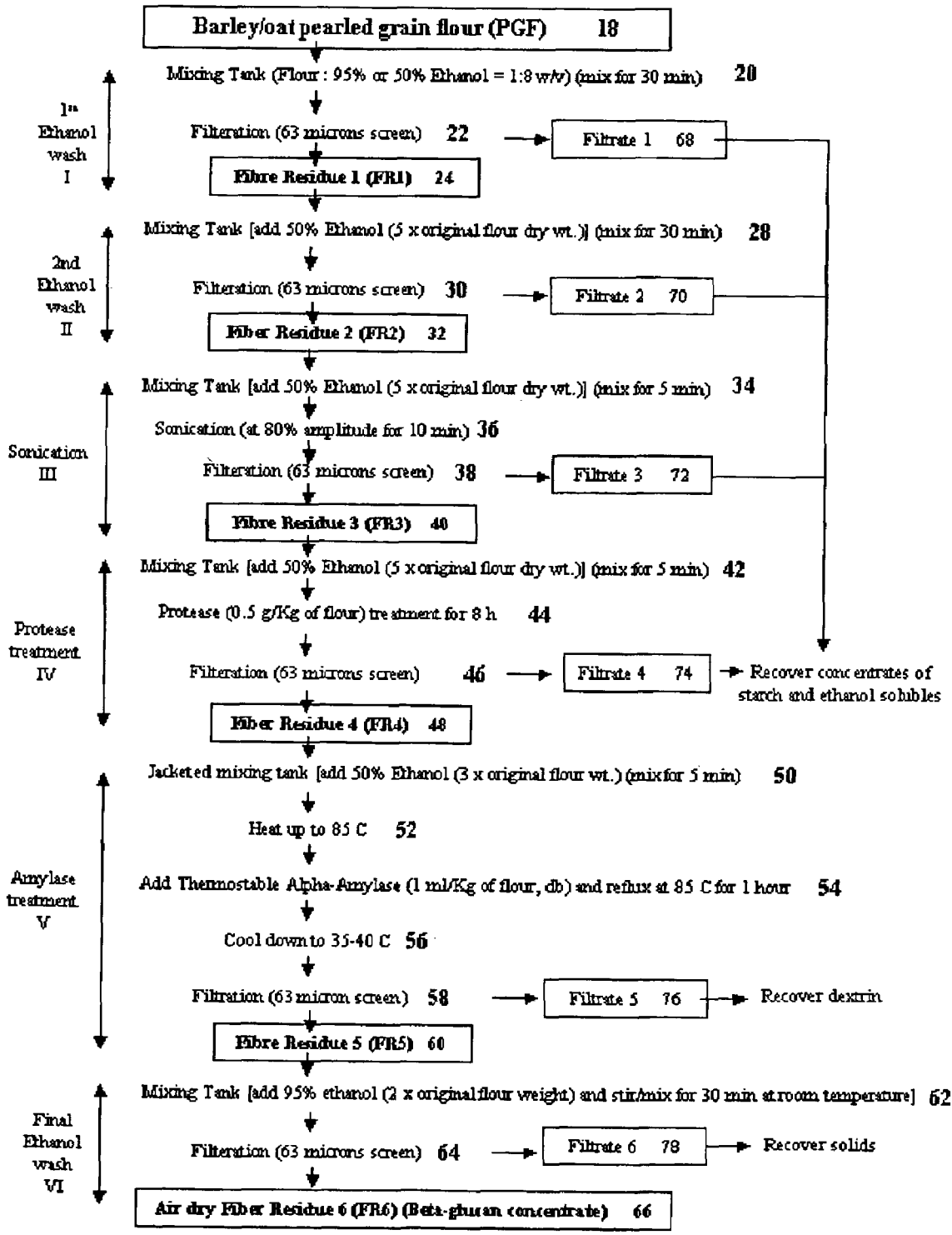
Figure 1B: Preparation of high viscosity beta-glucan concentrates

PREPARATION OF HIGH VISCOSITY BETA-GLUCAN CONCENTRATES

This invention is a continuation-in-part of U.S. patent application Ser. No. 10/380,739 filed Jul. 21, 2003 now U.S. Pat. No. 7,566,470 based on International Patent Application Serial No. PCT/CA01/01358 filed, Sep. 27, 2001.

FIELD OF THE INVENTION

This invention relates to methods for secondary processing of plant material and in particular for the recovery of valuable products such as fiber including beta-glucan, starch, protein and ethanol solubles from plant material containing starch and fiber. In particular, the invention relates to the preparation of high viscosity beta-glucan products through methods including alcohol slurrying, as well as enzyme treatments and/or sonication/sonification processing steps.

BACKGROUND OF THE INVENTION

Plant materials including grains contain a number of valuable components such as starch, protein, mixed linkage 1-4, 1-3 beta-D-glucan (hereinafter "beta-glucan" or "BG"), cellulose, pentosans, tocols, etc. These components, and products derived from these components, have many food and non-food uses. Consequently, there is a strong and continued industry interest for the processing of such plant materials.

Dietary fibre is generally accepted as having protective effects against a range of diseases predominant in Western developed countries including colorectal cancer, coronary heart disease, diabetes, obesity, and diverticular disease. The term 'dietary fiber' is commonly defined as plant material that resists digestion by the secreted enzymes of the human alimentary tract but may be fermented by the microflora in the colon. Increased fiber consumption is associated with lowering total serum cholesterol and LDL cholesterol, modifying the glycemic and insulinemic response and protecting the large intestine from disease. BG, a non-starch polysaccharide, is a water-soluble component of dietary fibre and thus contributes such health benefits.

BG has been extensively researched and has been found to have a number of positive health benefits including reducing cholesterol levels, regulating glycemic response, and immune system enhancement. In particular, consumption of beta-glucan is believed to increase the viscosity of intestinal contents, thus slowing down the movement of dietary cholesterol and glucose as well as bile acids towards the intestinal walls leading to reduced absorption. These benefits have led to the U.S. Food and Drug Administration (FDA) approving a health claim indicating that four daily servings of oat products containing 0.75 grams/serving of soluble oat fibre may reduce the risk of heart disease.

Cardio-Vascular Disease (CVD) is considered the principal cause of death in all developed countries, being responsible for 20% of deaths worldwide.[1] In the United States 59.7% of people had some form of CVD in 1997,[2] and in Canada, 8 million people are estimated to be suffering from CVD.[3] An estimated 102 million American adults have total blood cholesterol levels of 200 milligrams per deciliter (mg/dL) and higher. Of these, about 41 million have levels of 240 mg/dL or above. In adults, total cholesterol levels of 240 mg/dL or higher are considered high risk. Levels from 200 to 239 mg/dL are considered borderline high risk. Low-density lipoprotein (LDL) cholesterol levels of 130 mg/dL or higher is associated with increased risk of coronary heart disease and occurs in approximately 45% of Americans. Approximately 18% of Americans have LDL cholesterol levels of 160 mg/dL or higher. High LDL cholesterol levels are associated with a higher risk of coronary heart disease (CHD).

[1] "Cardiovascular Disease: Epidemiology" *World Health Organization*, Oct. 4, 2000. (Online, cited Dec. 8, 2000) Available at: http://www.who.int/ncd/cvd/cvd_epi.htm
[2] "Cardiovascular Disease Statistics" *American Heart Association*, 2000 (Online cited Nov. 23, 2000). Available at; http://www.americanheart.org/Heart_and_Stroke_A_Z_Guide/cvds.html)
[3] "Health Matters: Incidence of Cardiovascular Disease" *Heart and Stroke Foundation of Canada*, 2000. (Online, cited Nov. 28, 2000) Available at: http://heartandstroke.ca/cgi-bin/English/Catalog/Public/bR.cgi?110100:::Incedence%20of%20Cardiovascular%20Disease%20:::158981323241:::100001:110100

Not only is CVD the number one cause of death, it also is the most expensive disease in most developed countries. In the U.S. in 2002, the disease cost $329.2 billion in direct and indirect costs. Direct costs were $199.5 billion, with drug costs totaling $31.8 billion.[4] Canadian cost statistics are only as recent as 1993, but at this time total CVD costs were $19.7 billion. Direct costs amounted to $7.3 billion, with drugs accounting for $1.6 billion of this total.[5] These statistics demonstrate the importance of reducing the risk of CVD through dietary means. Increased consumption of soluble fiber, especially through the incorporation of beta-glucan concentrate as an ingredient into a variety of food products can contribute significantly towards this goal. However, it is crucial for the beta-glucan to have high-viscosity characteristics to achieve the claimed health benefits since there is growing evidence that links health benefits of beta-glucan to its viscosity.

[4] "Economic Costs of Cardiovascular Diseases" *American Heart Association*, 2002. 2002 Heart and Stroke Statistical Update.
[5] "The Changing Face of Heart Disease and Stroke in Canada 2000" *Heart and Stroke Foundation of Canada*, 2000. (Online, cited Nov. 29, 2000). Available at: http://www.hc-sc.gc.ca/hbp/lddc/bcrdd/hdsc2000/index.html Until now, BG has been restricted to high value markets such as cosmetics, medical applications, and health supplements due to the high cost of extraction, which has prohibited its use as an ingredient in the food industry. Current food products in the marketplace contain low concentrations of BG, requiring consumption of unrealistic amounts of such products in order to satisfy the parameters of the health claim.

In the extraction of BG from grains, a number of investigations at laboratory and pilot scale have been carried out on the fractionation of these grains including barley. In general, conventional processes utilize water, acidified water and/or aqueous alkali (i.e. NaOH, $Na_2CO_3$ or $NaHCO_3$) as solvents for the slurrying of whole cracked barley, barley meal (milled whole barley) or barley flour (roller milled barley flour or pearled-barley flour). These slurries are then processed by techniques such as filtration, centrifugation and ethanol precipitation to separate a slurry into various components. This conventional process for barley fractionation has a number of technical problems and whilst realizing limited commercial feasibility has been limited by the expense of the product particularly for food applications.

In particular, technical problems arise because the beta-glucan in barley flour is an excellent water-binding agent (a hydrocolloid) and as such, upon addition of water (neutral, alkali or acidic environment), the beta-glucan hydrates and tremendously thickens (increases the viscosity) the slurry. This thickening imposes many technical problems in the further processing of the slurry into pure barley components (i.e. starch, protein, fiber, etc.), including clogging of the filter during filtration and inefficient separation of flour components during centrifugation.

Usually, these technical problems are minimized, if not eliminated, by the addition of a substantial quantity of water to the thick/viscous slurry in order to dilute and bring the viscosity down to a level where further processing can be carried out. However, the use of high volumes of water leads to several further problems including increased effluent water volumes and the resulting increased disposal costs. In addition, the beta-glucan, which solubilizes and separates with the supernatant (water) during centrifugation, is usually recovered by precipitation with ethanol. This is done by the addition of an equal volume of absolute ethanol into the supernatant. After the separation of precipitated beta-glucan, the ethanol is preferably recovered for recycling. However, recovery requires distillation, which is also a costly operation from an energy usage perspective.

Furthermore, the aqueous alkali solubilization and subsequent precipitation of beta-glucan in ethanol (and centrifugation steps in between) is believed to contribute to the breakdown of the beta-glucan chains that results in a lower-grade, lower-viscosity beta-glucan product.

Still further, the use of these past techniques also is believed to support both the growth of microorganisms and increased enzyme activity that may contribute to hydrolysis of the beta-glucan chains. These problems are particularly manifested in larger batch operations where it may become difficult to control enzyme activity and thus lead to problems of batch-to-batch consistency.

Accordingly, there is a need for efficient processes for the fractionation of grains that overcomes the particular problems of slurry viscosity and water-usage. Moreover, there is a need for a process that provides a high purity, high-viscosity beta-glucan product in a close to natural state wherein the BG product has decreased starch and protein content.

Thus, there continues to be a need for techniques which improve the yield and quality of beta-glucan products extracted from the cell walls of grains including oats and barley that overcome problems of water-based extraction techniques.

A review of the prior art reveals that beta-glucan products having improved rheological properties have not been disclosed.

Moreover, sonication/sonification/ultrasonication/ultrasonification (hereinafter "sonication", "ultrasonication" and "US") techniques have not been applied to processes for the extraction of beta-glucan from barley and oats in an alcohol slurry.

For example, while the use of ultrasonication has been described in the production of konnyaku powder (See Kimura, T., Sugahara, T and Goto, M. 2000. Improvement of a method for production of konnyaku powder using ultrasonic treatment. Journal of the Japanese Society for Food Science and Technology (Nippon Shokuhin Kagaku Kogaku Kaishi). 47 (8):604-612), this reference is silent with respect to the extraction of beta glucan.

SUMMARY OF THE INVENTION

In accordance with the invention, a fractionation technology produces BG concentrate that maintains high quality functional characteristics including improved viscosity characteristics. In the context of this invention, improved viscosity characteristics of BG relates to the increased viscosity or high viscosity of solutions of fiber residues of BG prepared in accordance with the methodologies of the invention in comparison to the viscosity characteristics of BG solutions prepared in accordance with the prior art wherein both solutions incorporate equivalent concentrations of BG.

The process greatly reduces production time and improves process efficiency, therefore realizing significant cost savings in the extraction and purification of BG. High BG varieties of grains increase the yield of BG extracted thus also reducing the overall cost of extraction and purification.

More specifically and in accordance with the invention, there is provided a method of preparing a beta-glucan (BG) product comprising the steps of:
a) mixing a flour and an alcohol to form a flour/alcohol slurry;
b) separating a fiber residue from the alcohol, wherein the fiber residue has a high BG content;
c) subjecting the fiber residue from step b) to at least one additional treatment step, the additional treatment step including mixing the fiber residue from step b) with an alcohol to form a fiber residue/alcohol slurry and subjecting the fiber residue/alcohol slurry to a sonication, protease or amylase treatment step or a combination of a sonication, protease or amylase treatment step and thereafter separating a final fiber residue from the fiber residue/alcohol slurry.

Furthermore, and in various embodiments the method includes a sonication treatment step, a sonication and protease treatment step, a sonication and amylase treatment step, a protease and amylase treatment step or a sonication, protease and amylase treatment step.

The invention also provides a method of preparing high viscosity BG products whose viscosities can be characterized as high viscosity by comparing solubilized BG fiber residues prepared in accordance with the above methodology in comparison to the viscosities of solubilized BG fiber residues derived from prior art methods.

More specific embodiments of the invention include providing a final fiber residue having a composition wherein the BG content is greater than 25% (w/w, dry matter basis) for particular varieties of source flour and greater than 35% (w/w, dry matter basis) for other varieties of source flour. Furthermore, the invention provides a method wherein the final fiber residue has a composition having less than 40% (w/w, dry matter basis) starch content and preferably less than 20% (w/w, dry matter basis) starch content.

The invention also provides fiber residues having a high beta-glucan (BG) content and a high viscosity, the high viscosity characterized wherein a 0.5% (w/w) BG solution prepared from the fiber residue has a viscosity greater than 200 mPa·s, greater than 350 mPa·s or greater than 500 mPa·s at a shear rate of 12.9 $s^{-1}$ at 20° C.

In one embodiment the BG content of the fiber residue is preferably greater than 35% (w/w).

The method preferably utilizes pearled grains wherein the pearling is greater than 20% and more preferably 25-40%. Flour particle sizes are preferably less than 250 microns.

When subjected to a protease or amylase treatment, it is preferred that the fiber residue/alcohol slurry is incubated with 0.1-3% (w/w, protein or starch weight basis) of a protease or amylase and wherein the protease may be selected from any one of or a combination of papain, bromelain, microbial protease and the amylase may be selected from any one of or a combination of microbial, plant or animal amylase.

When subjected to a sonication treatment step it is preferred that the fiber residue/alcohol slurry be sonicated for 3-15 minutes at a power level of 2.5-3.5 kW or at a power selected to minimize fragmentation of BG.

In another embodiment, the invention provides for the use of ultrasonication to produce a beta glucan product high in beta glucan content from a slurry of a flour and an alcohol.

In a more specific embodiment, the invention provides a method of preparing a high viscosity beta-glucan product comprising the steps of:
a) mixing a flour in aqueous ethanol to produce a first flour-alcohol slurry;
b) filtering the flour-alcohol slurry to produce an alcohol filtrate and a first fiber residue;

c) mixing the first fiber residue with aqueous ethanol to form a fiber residue/alcohol slurry;

d) filtering the fiber residue/alcohol slurry to produce a second alcohol filtrate and a second fiber residue containing high viscosity beta-glucan;

wherein either or both of the flour/alcohol or fiber residue/alcohol slurries are subjected to an ultrasonication treatment.

In further embodiments, the aqueous alcohol in steps a and c is 8-100% (w/w), 40-95% (w/w) or 50% (w/w) and/or the flour:aqueous ethanol is 1:5 to 1:8 (w/w).

In a still further embodiment, the invention provides a method of controlling the degree of fragmentation of beta-glucan (BG) within an aqueous alcohol BG fiber residue solution by subjecting the aqueous alcohol BG fiber residue solution to a sonication treatment wherein the ratio of water:alcohol in the solution is selected on the basis of the desired fragmentation of beta glucan within the solution wherein a lower water:alcohol ratio is selected to decrease the level of fragmentation of beta glucan within the solution and a higher water:alcohol ratio is selected to increase the level of fragmentation of beta glucan within solution.

BRIEF DESCRIPTION OF THE DRAWINGS

The invention is described with reference to the following drawings wherein:

FIG. 1B is an overview of preferred methodologies for preparing improved beta-glucan products.

DETAILED DESCRIPTION OF THE INVENTION

Figure 1A:
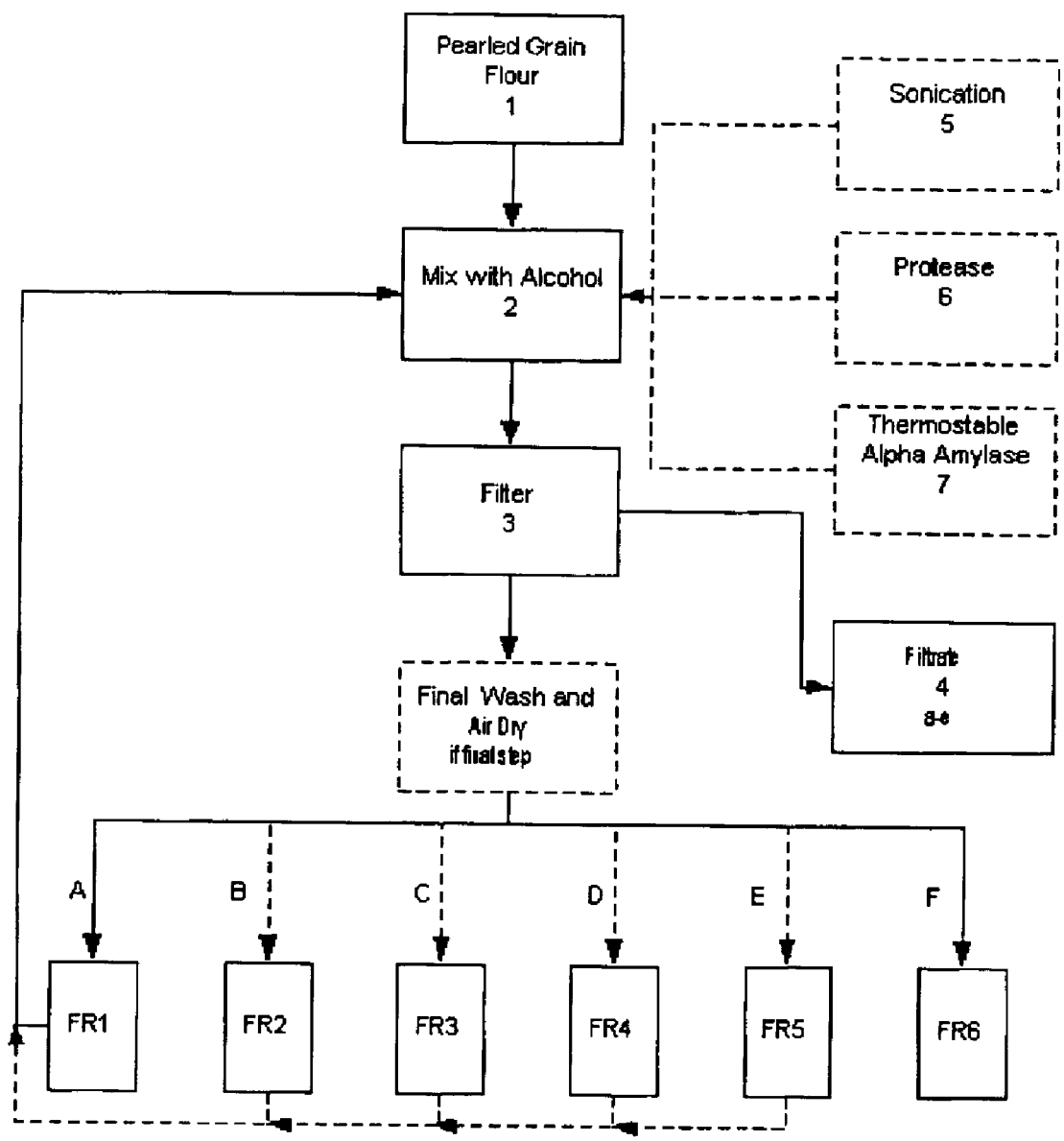
FIG. 1A is an overview of the methodologies of the invention for preparing improved beta-glucan products.

The invention is described with reference to FIGS. 1A and 1B. FIG. 1A is an overview of the methodologies of the invention for preparing improved beta-glucan products and FIG. 1B is an overview of preferred methodologies for preparing improved beta-glucan products.

With reference to FIG. 1A, pearl grain flour 1 is mixed with alcohol 2 to form a flour/alcohol slurry which may include optional sonication 5, protease 6 and amylase treatments. The slurry is filtered 3 to separate fiber residue (FR1) from the filtrate 4. The mixing and filtering steps are repeated as desired (pathways B-E) again with optional sonication 5, protease 6 and amylase 7 treatments to produce fiber residues FR2-FR6 and filtrates b-e.

More specifically and with reference to FIG. 1B, a preferred methodology 10 for preparing BG fiber residues is described as general steps I-VI and detailed steps 18-78. Step I refers to a first ethanol wash, Step II refers to a second ethanol wash, Step III refers to a sonication step, Step IV refers to a protease treatment step, Step V refers to an amylase treatment step and Step VI refers to a final ethanol wash. It is understood that in accordance with the invention that Step I can be combined with any combination of Steps II-V with it being preferred that Step VI complete the process.

The following describes three studies undertaken in the preparation of high viscosity BG fiber residues from pearled grain flours of CDC-Candle barley, HiFi oats and Antoine to determine the effect of individual processing steps on the yield of fiber residue (FR) as well as the purity of the beta-glucan within the FR.

Materials and Methodology

Barley and oat flours were prepared by pearling whole barley or oat groats (10-35%) and milling the pearled grains to <250 μm using a pin mill.

Study #1: The Effect of Various Processing Steps of FIG. 1B on the Viscosity of Fiber Residues Prepared at A) a Laboratory Scale and B) a Pilot Plant Scale.

A) Laboratory Scale Study

The following fibre residues were prepared in the lab according to selected steps in FIG. 1B using 100 g of flour as a starting material:

Blank (ethanol washing) (FIG. 1B—Steps I, II, and VI)—Two washings in 50% ethanol (30 min each), recovery of fiber residue and final wash in absolute ethanol.

US (Ultrasonication) (FIG. 1B—Steps I, II, III and VI)—Two ethanol washings as similar to blank, recovery of fiber residue, US treatment for 10 min in 50% ethanol, recovery of fiber residue and final absolute ethanol wash. One methodology of ultrasonication is explained in greater detail below.

PT (protease treatment) (FIG. 1B—Steps I, II, IV and VI)—Two ethanol washings as similar to blank, recovery of fiber residue, protease treatment for 8 hours in 50% ethanol, recovery of fiber residue and final absolute ethanol wash.

US+PT (US and PT) (FIG. 1B—Steps I, II, III, IV and VI)—Two ethanol washings as similar to blank, recovery of fiber residue, US treatment for 10 min, protease treatment for 8 hours, recovery of fiber residue and final absolute ethanol wash.

PT+TT (PT and thermostable alpha-amylase treatment (TT)) (FIG. 1B—Steps I, II, IV, V and VI)—Two ethanol washings as similar to blank, protease treatment to the fiber residue for 8 hours, recovery of fiber residue, TT treatment to the fiber residue for 1 hour in 50% ethanol, recovery of fiber residue and final absolute ethanol wash.

US+PT+TT (US, PT and TT treatments) (FIG. 1B—Steps I, II, III, IV, V and VI)—Two ethanol washings as similar to blank, US treatment for 10 min, recovery of fiber residue, protease treatment to the fiber residue for 8 hours, recovery of fiber residue, TT treatment to the fiber residue for 1 hour, recovery of fiber residue and final absolute ethanol wash.

In addition, a high purity BG sample (78% w/w, dry wt basis) obtained from barley flour was prepared in the laboratory using aqueous alkali extraction and ethanol precipitation methodology of the prior art (referred to hereinafter as LAB gum). This process consists of mixing flour and water and adjusting the pH to an alkali pH (preferably pH 9) through addition of sodium carbonate. The extraction is continued for 1 hour at 55° C. The pH of the mixture is adjusted to pH 4.5 to precipitate protein, which is then separated from the solution by centrifugation. BG in the supernatant is precipitated through the addition of absolute ethanol and the BG is recovered by centrifugation and subsequently dried.

Beta-Glucan Solution Preparation

The dried fiber residue (beta glucan concentrate) was then used in the preparation of aqueous beta glucan solutions (0.5%, w/w). The amount of dried fiber residue required was calculated to contain 100 mg of beta-glucan based on the beta-glucan content of the fiber residues determined according to the Megazyme procedure (Megazyme International Inc., Bray, Ireland). A beaker containing 20 g water was placed on a heater-stirrer. The fiber residue was mixed into the water with vigorous stirring. Heat stable amylase (35 μL of Termamyl 120 L obtained from Novozyme, Toronto, Ontario) enzyme was added to hydrolyze remaining starch and minimize the influence of starch on subsequent viscosity measurements.

The beaker was covered with Al-foil and the contents of the beaker was quickly brought to boiling and stirred on the hot plate for ≧1 hr at ~80° C. The solution was then cooled, weight adjusted with distilled water to compensate for any loss during heating to a final beta glucan concentration of 0.5% (w/w), stirred for about 30 sec and transferred into pasteurized 50 mL tubes. The tubes were then centrifuged (Centra MP4, International Equipment Company, USA) at 4000 rpm for 10 min and the supernatant used for viscosity measurements.

Viscosity Measurements

The viscosity of the supernatant was measured using a PAAR Physica UDS rheometer (Glenn Allen, Va.). The supernatant (7.05 g±0.01 g) was pipetted directly into a DG 27 cup and viscosity was determined at 1-100 rpm (shear rate=1.29-129 s$^{-1}$) and 20° C. in the Controlled Shear Rate mode.

B) Pilot Scale Study

The pilot scale study prepared Candle barley and Antoine oat fiber residues using 5 kg and 200 kg batches of flour as the starting material in accordance with Steps I, II, III, V and VII as described above and with reference to FIG. 1B. Viscosity was determined according to the same methodology as for the laboratory study.

Study #2: Yield, Recovery (BG) and Composition of Fiber Residue as Influenced by the Degree of Pearling and Ultrasonication—Laboratory Study Candle barley and HiFi oat flours were used in this study. Grain pearling was performed to 10-35%. Fiber residues were prepared in the laboratory by ultrasonication according to Steps I, II, III and VI.

Fiber residue yield is based on the weight of fiber residue relative to the weight of the starting flour. BG recovery is based on the weight of BG in the recovered fiber residue relative to the weight of BG in the starting flour. The BG, protein and starch content of the raw and recovered fiber residue were determined by standard techniques (AACC 2000) and is the wt % of each within the recovered fiber residue.

Study #3: Viscosity of Beta-Glucan in Oat and Barley Fiber Residues as Influenced by Ultrasonication when Carried Out in Aqueous-Ethanol Slurry and 100%-Aqueous Solution Candle barley and HiFi oat flours were used in this study. Grain pearling was performed to 30%. Fiber residues were prepared in the laboratory by ultrasonication according to Steps I, II, III and VI and viscosity determination was performed as described above. In order to perform the ultrasonication of BG in 100% aqueous media, the dry fiber residue obtained through Steps I, II, III and VI was solubilized in water to prepare a uniform solution and ultrasonication performed at 80% amplitude for 10 minutes.

Results and Discussion

Study #1 (Tables 1 and 2)

Viscosity of fresh solutions (containing 0.5% BG (w/w)) (Table 1) prepared in the laboratory from fiber residues obtained from the above methodologies as in FIG. 1B (two steps of 50% ethanol wash (blank) and various combinations of US, protease treatment (PT) and amylase treatment (TT) steps) were determined. The viscosities of two other beta-glucan gums (commercial oat gum and barley LAB gum) obtained with conventional aqueous alkali extraction are also shown for comparison purposes. The commercial oat gum had a purity 58% BG (w/w, dry matter basis) and the high viscosity barley LAB gum had a purity of 78% BG (w/w, dry matter basis).

The viscosities of Candle barley, HiFi oat, and Antoine oat fiber residues as shown in Table 1 were superior to high viscosity LAB gum and commercial oat gum. As expected, the fiber residue solutions exhibited pseudo-plastic or shear-thinning behaviour, where the viscosity drops with increased shear rate from 12.9 s$^{-1}$ to 129 s$^{-1}$. At 129 s$^{-1}$ the viscosity of fiber residues approached that of LAB gum.

The data in Table 2 shows the aqueous solution viscosities of fibre residue (combination of US and TT treatments) obtained in the pilot plant from Candle barley and Antoine oat flours. These results are comparable to those obtained from the laboratory study indicating that there is no damage to BG viscosity during scale-up using industrial equipment.

Study #2 (Tables 3 and 4)

Tables 3 and 4 show yield, recovery (BG) and composition of fiber residue as influenced by the degree of pearling and ultrasonication for HiFi Oat and Candle Barley, respectively.

The yield of fiber residue (flour dry weight basis) showed a marginal decrease (<1.5%) as the degree of pearling increased. The recovery of beta-glucan ranged from 80-94%. The β-glucan content of the fiber residue increased by up to 2.4% as the degree of pearling increased. With an increased level of pearling, protein content decreased in the fiber residue for both oat and barley, whereas the starch content increased in barley but was marginally changed in oat.

Thus, an increased level of pearling does not show a significant advantage from a yield perspective. However, the level of pearling showed a noticeable effect on the color/brightness of the fiber residue wherein samples at greater than 25% pearling were substantially brighter than samples with less than 20% pearling.

Sonicated samples showed substantially higher (up to 12%) beta-glucan content as compared to the blank samples (produced without US). As shown in Table 3, the Hi-Fi flour sample prepared from 35% pearled grain resulted in a fiber residue containing 28.4% (w/w) beta-glucan whereas the comparable sonicated fiber residue had 40.1% (w/w) beta glucan. Similar improvements in BG concentration were observed with Candle barley upon sonication as shown in Table 4.

These results demonstrate the effectiveness of ultrasonication in concentrating beta-glucan with high recovery. It is believed that ultrasonication is particularly effective in breaking up the plant cell wall structure thereby enhancing the separation of beta-glucan from the rest of the cell materials in a form that is close to native state.

Study #3 (Table 5)

Table 5 shows the effect of sonication on the viscosities of BG solutions when carried out in aqueous ethanol slurry and 100% aqueous solutions.

Fiber residues prepared by ultrasonication in 50% ethanol media had comparable viscosities to those of the blanks, indicating that ultrasonication is not detrimental to beta-glucan quality in the presence of ethanol. However, if ultrasonication is applied in the absence of ethanol but with 100% water, where beta-glucan is completely hydrated and solubilized, then there was a significant decrease in viscosity indicating that the beta-glucan molecule in aqueous media is highly sensitive to damage, perhaps being fragmented upon sonication. Thus, the use of sonication is also effective as a tool in controlling the viscosity of the beta-glucan by selection of the slurry media. That is, selection of a high water-content slurry media results in a lower viscosity product through the sonication treatment whereas a high alcohol content slurry media results in a higher viscosity product.

TABLE 1

Aqueous solution viscosity of fiber residue obtained in the laboratory from Candle barley, Hi Fi and Antoine oat flours[1]. Concentration of solution used for viscosity measurements is 0.5% beta-glucan by weight.

| | Viscosity (mPa · s) at 20° C. | |
|---|---|---|
| Variety and Treatment | @ shear rate 12.9 s$^{-1}$ | @ shear rate 129 s$^{-1}$ |
| Candle barley | | |
| Blank | 617 | 168 |
| US | 530 | 147 |
| PT | 490 | 141 |
| US + PT | 525 | 140 |
| PT + TT | 396 | 125 |
| US + PT + TT | 500 | 147 |
| HiFi oat | | |
| Blank | 736 | 145 |
| US | 960 | 171 |
| PT | 551 | 136 |
| US + PT | 443 | 117 |

TABLE 1-continued

Aqueous solution viscosity of fiber residue obtained in the laboratory from Candle barley, Hi Fi and Antoine oat flours[1]. Concentration of solution used for viscosity measurements is 0.5% beta-glucan by weight.

| | Viscosity (mPa · s) at 20° C. | |
|---|---|---|
| Variety and Treatment | @ shear rate 12.9 s$^{-1}$ | @ shear rate 129 s$^{-1}$ |
| PT + TT | 646 | 126 |
| US + PT + TT | 714 | 146 |
| Antoine oat | | |
| Blank | 700 | 136 |
| US | 586 | 115 |
| PT | 468 | 117 |
| US + PT | 442 | 124 |
| PT + TT | 520 | 104 |
| US + PT + TT | 526 | 110 |
| LAB Gum[2] | 192 | 108 |
| Commercial Oat Gum[3] | 33 | 31 |

[1]Prepared from ~30% pearled grains
[2]High-viscosity barley beta-glucan gum obtained in the lab using aqueous alkali extraction had a beta-glucan purity of 78% (w/w)
[3]Commercial Oat Gum had a beta-glucan purity of 58% (w/w)

TABLE 2

Aqueous solution viscosity of fiber residue obtained in the pilot plant from Candle barley and Antoine oat flours[1]. Concentration of solution used for viscosity measurements is 0.5% beta-glucan by weight.

| | Viscosity (mPa · s) at 20° C. | |
|---|---|---|
| Variety and Treatment | @ shear rate 12.9 s$^{-1}$ | @ shear rate 129 s$^{-1}$ |
| 5 kg batch | | |
| Candle barley US + TT | 368 | 109 |
| Antione oat US + TT | 538 | 124 |
| 200 kg batch | | |
| Candle barley US + TT | 557 | 140 |
| Antione oat US + TT | 553 | 132 |
| LAB Gum[2] | 192 | 108 |
| Commercial Oat Gum[3] | 33 | 31 |

[1]Prepared from ~30% pearled grains
[2]High-viscosity barley beta-glucan gum obtained in the lab using aqueous alkali extraction had a beta-glucan purity of 78% (w/w)
[3]Commercial Oat Gum had a beta-glucan purity of 58% (w/w)

TABLE 3

Yield, Recovery (BG) and Composition of HiFi oat fiber residue

| Treatments (Degree of pearling, %) | β-Glucan in flour, % (w/w) | Yield[1] % | Recovery[2] % | Composition of fiber residue (%, w/w, dry matter basis) | | |
|---|---|---|---|---|---|---|
| | | | | β-Glucan | Protein | Starch |
| Without Ultrasonication (Blank) | | | | | | |
| 15.2 | 5.9 | 19.7 | 91.6 | 28.8 | 20.4 | 27.1 |
| 23.9 | 5.9 | 18.9 | 88.7 | 29.2 | 20.7 | 29.6 |
| 30.0 | 6.2 | 19.4 | 85.0 | 28.0 | 20.3 | 30.7 |
| 35.3 | 6.0 | 18.8 | 85.5 | 28.4 | 19.8 | 28.2 |
| With Ultrasonication | | | | | | |
| 15.2 | 5.9 | 13.6 | 84.9 | 38.6 | 18.2 | 18.1 |
| 23.9 | 5.9 | 13.5 | 85.8 | 39.8 | 19.1 | 16.3 |
| 30.0 | 6.2 | 13.2 | 84.2 | 41.2 | 18.4 | 18.8 |
| 35.3 | 6.0 | 12.5 | 80.1 | 40.1 | 17.9 | 15.4 |

[1]Yield = (wt. of fiber residue/wt. of starting flour) × 100
[2]Recovery = (wt. of β-glucan in fiber residue/wt. of β-glucan in starting flour) × 100 (Megazyme method)

TABLE 4

Yield, Recovery (BG) and Composition of Candle Barley fiber residue

| Treatments (Degree of pearling, %) | β-Glucan in flour, % (w/w) | Yield[1] % | Recovery[2] % | Composition of fiber residue (%, w/w dry matter basis) | | |
|---|---|---|---|---|---|---|
| | | | | β-Glucan | Protein | Starch |
| Without Ultrasonication (Blank) | | | | | | |
| 10.2 | 7.1 | 32.7 | 91.1 | 19.8 | 13.4 | 47.6 |
| 15.4 | 7.0 | 31.8 | 90.4 | 20.3 | 12.3 | 47.1 |
| 24.7 | 7.0 | 31.5 | 94.3 | 21.2 | 10.3 | 48.5 |
| 29.7 | 6.9 | 31.7 | 91.8 | 20.5 | 11.3 | 49.6 |
| 35.0 | 6.9 | 31.3 | 93.1 | 20.9 | 10.4 | 48.5 |
| With Ultrasonication | | | | | | |
| 10.2 | 7.1 | 22.2 | 87.0 | 27.9 | 13.0 | 33.4 |
| 15.4 | 7.0 | 21.7 | 90.5 | 29.8 | 12.3 | 36.8 |
| 24.7 | 7.0 | 21.5 | 91.9 | 30.2 | 10.2 | 34.2 |
| 29.7 | 6.9 | 21.4 | 90.2 | 29.7 | 11.1 | 36.1 |
| 35.0 | 6.9 | 20.8 | 90.3 | 30.3 | 10.1 | 39.9 |

[1]Yield = (wt. of fiber residue/wt. of starting flour) × 100
[2]Recovery = (wt. of β-glucan in fiber residue/wt. of β-glucan in starting flour) × 100

TABLE 5

Viscosity of fiber residue obtained from Candle barley and HiFi oat flours[1] after processing with and without sonication.

| | Viscosity (mPa · s) at 20° C. | |
|---|---|---|
| Variety and Treatment | @ shear rate 12.9 s$^{-1}$ | @ shear rate 129 s$^{-1}$ |
| Candle | | |
| Blank (no sonication) | 530 | 147 |
| Ultrasonication of flour slurry in aqueous EtOH media | 617 | 168 |
| Ultrasonication of aqueous beta-glucan solution | 25 | 14 |
| HiFi | | |
| Blank (no sonication) | 736 | 145 |
| Ultrasonication of flour slurry in aqueous EtOH media | 960 | 171 |
| Ultrasonication of aqueous beta-glucan solution | 32 | 12 |
| LAB Gum[2] | 192 | 108 |
| Commercial Oat Gum[3] | 33 | 31 |

[1]Prepared from ~30% pearled grains
[2]High-viscosity barley beta-glucan gum obtained in the lab using aqueous alkali extraction had a beta-glucan purity of 78% (w/w)
[3]Commercial Oat Gum had a beta-glucan purity of 58% (w/w)

The invention claimed is:

1. The method of concentrating beta-glucans (BG) from a plant material flour comprising the steps of:
   a) mixing and incubating a plant material flour with a solution of ethanol and water wherein the ethanol is at a concentration of 40-95% (v/v) in the water to form a flour/ethanol slurry without beta-glucan being solubilized within the flour/ethanol slurry;
   b) separating some protein and starch from the flour/ethanol slurry to create a fiber residue having a reduced starch and protein content from the flour/ethanol slurry, wherein the fiber residue has a higher BG content than the plant material flour;
   c) subjecting the fiber residue from step b) to at least one additional treatment step, the additional treatment step including mixing the fiber residue from step b) with a solution of ethanol and water wherein the ethanol is at a concentration of 40-95% (v/v) in the water to form a fiber residue/ethanol slurry and subjecting the fiber residue/ethanol slurry to a sonication, protease or amylase treatment step or a combination of a sonication, protease or amylase treatment step without beta-glucan being solubilized within the flour/ethanol slurry and thereafter separating a final fiber residue from the fiber residue/ethanol slurry
   wherein the final fiber residue has a higher beta-glucan content than the fiber residue from step b).

2. The method as in claim 1 wherein step c) includes a sonication treatment step wherein the sonication treatment step is conducted at a power selected to minimize fragmentation of BG while maximizing the release of starch and protein from the cell network of the flour.

3. The method as in claim 2 wherein step c) includes a sonication treatment step and wherein step c) is repeated with a protease treatment step.

4. The method as in claim 3 wherein step c) is repeated with an amylase treatment step.

5. The method as in claim 2 wherein step c) includes a sonication treatment step and wherein step c) is repeated with an amylase treatment step.

6. The method as in claim 1 wherein the final fiber residue has a composition wherein the BG content is greater than 25% (w/w, dry matter basis).

7. A method as in claim 6 wherein the final fiber residue has a composition wherein the beta-glucan content is greater than 35% (w/w, dry matter basis).

8. The method as in claim 1 wherein the final fiber residue has a composition having less than 40% (w/w, dry matter basis) starch content.

9. The method as in claim 1 wherein the final fiber residue has a composition having less than 20% (w/w, dry matter basis) starch content.

10. The method as in claim 1 wherein the plant material flour for step a) is prepared from a pearled grain wherein the pearling is greater than 20%.

11. The method as in claim 10 wherein the pearling is 25-40%.

12. The method as in claim 1 wherein the plant material flour for step
   a) has a particle size less than 250 microns.

13. The method as in claim 1 wherein during step c), the fiber residue/ethanol slurry is incubated with greater than 0.1% (w/w, protein or starch weight basis) of a protease or amylase.

14. The method as in claim 1 wherein during step c), the fiber residue/ethanol slurry is incubated with 0.1-3% (w/w, protein or starch weight basis) of a protease or amylase.

15. The method as in claim 13 wherein the protease is selected from any one of or a combination of a plant, animal or microbial protease and the amylase is selected from any one of or a combination of microbial, plant or animal amylase.

16. The method as in claim 2 wherein the sonication treatment step includes subjecting the fiber residue/ethanol slurry to sonication at a power level of greater than 2.5 kW.

17. The method as in claim 2 wherein the sonication treatment step includes subjecting the fiber residue/ethanol slurry to sonication for 3-15 minutes at a power level of 2.5-3.5 kW.

18. The method as in claim 1 wherein the ethanol is at a concentration in water of 50% (v/v).

19. The method as in claim 1 wherein the flour:ethanol and water solution is 1:5 to 1:8 (w/w).

20. The method as in claim 1 wherein the final fiber residue has a high viscosity, the high viscosity characterized wherein a 0.5% (w/w) BG solution prepared from the final fiber residue has a viscosity greater than 200 mPa·s at a shear rate of $12.9 \text{ s}^{-1}$ at 20° C.

21. The method as in claim 1 wherein the final fiber residue has a high viscosity, the high viscosity characterized wherein a 0.5% (w/w) BG solution prepared from the fiber residue has a viscosity greater than 350 mPa·s at a shear rate of $12.9 \text{ s}^{-1}$ at 20° C.

22. The method as in claim 1 wherein the final fiber residue has a high viscosity, the high viscosity characterized wherein a 0.5% (w/w) BG solution prepared from the fiber residue has a viscosity greater than 500 mPa·s at a shear rate of $12.9 \text{ s}^{-1}$ at 20° C.

23. The method of concentrating beta-glucans from a plant material flour comprising the steps of: a) mixing a plant material flour in a solution of ethanol and water wherein the ethanol is at a concentration of 40-100% (v/v) in the water to produce a first flour-ethanol slurry without beta-glucan being solubilized within the first flour/ethanol slurry; b) filtering the flour-ethanol slurry to produce an alcohol filtrate and a first fiber residue; c) mixing the first fiber residue in a solution of ethanol and water wherein the ethanol is at a concentration of 40-100% (v/v) in the water to form a fiber residue/ethanol slurry without beta-glucan being solubilized within the fiber residue/ethanol slurry; d) filtering the second fiber residue/ethanol slurry to produce a second alcohol filtrate and a second fiber residue containing beta-glucan; wherein either or both of the flour/ethanol or fiber residue/ethanol slurries are subjected to an ultrasonication treatment.

24. The method as in claim 23 wherein the method further comprises subjecting the second fiber residue to a further ethanol and water wash and filtering step.

25. The method as in claim 23 wherein the concentration of ethanol in water steps a and c is 50% (v/v).

26. The method as in claim 23 wherein the flour:ethanol and water solution is 1:5 to 1:8 (w/w).

* * * * *